United States Patent
Brodin et al.

(10) Patent No.: US 6,727,062 B1
(45) Date of Patent: Apr. 27, 2004

(54) IDENTIFICATION OF TARGET STRUCTURES E.G. IN VIVO SELECTION METHOD FOR A PHAGE LIBRARY

(75) Inventors: Thomas Brodin, RÅÅ (SE); Jesper Tordsson, Lund (SE); Pia Jasmine Karlström, Lund (SE)

(73) Assignee: Active Biotech AB, Lund (SE)

( * ) Notice: Subject to any disclaimer, the term of this patent is extended or adjusted under 35 U.S.C. 154(b) by 0 days.

(21) Appl. No.: 09/365,241

(22) Filed: Jul. 30, 1999

Related U.S. Application Data (63) Continuation of application No. PCT/SE98/00083, filed on Jan. 21, 1998.

(30) Foreign Application Priority Data

Jan. 31, 1997 (SE) ............................................. 9700291

(51) Int. Cl.$^7$ ............................ C12Q 1/68; C12Q 1/70; C07K 16/00; C12P 21/08; G01N 33/543

(52) U.S. Cl. .............. 435/6; 435/4; 435/5; 435/DIG. 2; 435/DIG. 3; 435/DIG. 35; 435/DIG. 40; 530/387.1; 530/387.3

(58) Field of Search ...................... 435/4, 5, 6, DIG. 2, 435/DIG. 3, DIG. 35, DIG. 40; 530/387.1, 387.3; 436/873

(56) References Cited

U.S. PATENT DOCUMENTS

| | | | |
|---|---|---|---|
| 5,622,699 A | | 4/1997 | Ruoslahti et al. .......... 424/93.6 |
| 6,117,632 A | * | 9/2000 | O'Mahony ...................... 435/6 |

FOREIGN PATENT DOCUMENTS

| | | |
|---|---|---|
| EP | 0773441 A1 | 5/1997 |
| WO | WO92/15679 | 9/1992 |
| WO | WO94/26787 | 11/1994 |
| WO | WO94/28424 | 12/1994 |
| WO | WO97/17614 | 5/1997 |
| WO | WO97/22972 | 6/1997 |

OTHER PUBLICATIONS

"In vivo selection of a lupus phage–display Fv library", W.V. Williams et al., Abstracts from *Immunotechnology*, vol. 2, No. 4 (1996) p. 295–296.

"In vivo selection of a lupus phage–display Fv library", W.V. Williams et al., *Dialog*, Abstract No. 13438353 (1996).

"Autoimmune derived combinatorial phage display libraries: methods in construction of and affinity selection for anti–RNA Fabs", Marie T. Marchbank et al., *Nucleic Acids Symposium Series*, No. 33 (1995) pp. 120–122.

"High Affinity, Thyroid–Specific Human Autoantibodies Displayed on the Surface of Filamentous Phage Use V Genes Similar to Other Autoantibodies", Stefano Portolano et al., *The Journal of Immunology*, vol. 151, No. 5 (Sep. 1, 1993) pp. 2839–2851.

"Toward cell–targeting gene therapy vectors: Selection of cell–binding peptides from random peptide–presenting phage libraries", Michael A. Barry et al., *Nature Medicine*, vol. 2, No. 3 (Mar. 1996) pp. 299–305.

"A melanonia–specific $V_R$ antibody cloned from a fusion phage library of a vaccinated melanoma patient", Xiaohong Cai et al., *Proc. Natl. Acad. Sci. USA*, vol. 93 (Jun. 1996) pp. 6280–6285.

"Making Antibodies by Phage Display Technology", Greg Winter et al., *Annu. Rev. Immunol.*, vol. 12 (1994) pp. 433–455.

"Combinatorial infection and in vivo recombination: a strategy for making large phage antibody repertoires", Peter Waterhouse et al., *Nucleic Acids Research*, vol. 21, No. 9 (1993) pp. 2265–2266.

"Isolation of high affinity human antibodies directly from large synthetic repertoires", Andrew D. Griffiths et al., *The EMBO Journal*, vol. 13, No. 14 (1994) pp. 3245–3260.

"An Antibody Fragment from a Phage Display Library Competes for Ligand Binding to the Low Density Lipoprotein Receptor Family and Inhibits Rhinovirus Infection", Regina A. Hodits et al., *The Journal of Biological Chemistry*, vol. 270, No. 41 (Oct. 13, 1995) pp. 24078–24085.

"Phage antibodies: filamentous phage displaying antibody variable domains", John McCafferty et al., *Nature*, vol. 348 (Dec. 6, 1990) pp. 552–554.

"Assembly of combinatorial antibody libraries on phage surfaces: The gene III site", Carlos F. Barbas, III et al., *Proc. Natl. Acad. Sci. USA*, vol. 88 (Sep. 1991) pp. 7978–7982.

"Clonal Selection and Amplification of Phage Displayed Antibodies by Linking Antigen Recogniton and Phage Replication", Marta Dueñas et al., *Biotechnology*, vol. 12 (Oct. 1994) pp. 999–1002.

"Use of Living Columns to Select Specific Phage Antibodies", Andrew Bradbury et al., *Biotechnology*, vol. 11 (Dec. 1993) pp. 1565–1569.

"Human Antibody Fragments Specific for Human Blood Group Antigens from a Phage Display Library", James D. Marks et al., *Biotechnology*, vol. 11 (Oct. 1993) pp. 1145–1149.

(List continued on next page.)

*Primary Examiner*—Padmashri Ponnaluri
(74) *Attorney, Agent, or Firm*—Burns, Doane, Swecker & Mathis, L.L.P.

(57) ABSTRACT

The invention relates to a selection method and the products identified using the selection method which includes the steps of identifying one or more binding structures to a target structure using one or more libraries. The method includes the steps of reacting a first library with the displayed target structure to bind some of the binding structures to the displayed target structure, separating the displayed target structure and bound binding structures from unbound binding structures, and recovering bound or unbound binding structures. The bound or unbound binding structures can be amplified to create enriched libraries of binding structures. Binding structures thus identified are directed to target structures which are displayed in vivo and/or in situ.

34 Claims, 6 Drawing Sheets

OTHER PUBLICATIONS

"Rapid selection of cell subpopulation–specific human monoclonal antibodies from a synthetic phage antibody library", John De Kruif et al., *Proc. Natl. Acad. Sci, USA*, vol. 92 (Apr. 1995) pp. 3938–3942.

"Generation and selection of monoclonal antibodies, single–chain $F_v$ and antibody fusion phage specific for human melanoma–associated antigens", J.M. Kupsch et al., Melanoma Research, vol. 5 (1995) pp. 403–411.

"Anti–melanoma antibodies from melanoma patients immunized with genetically modified autologous tumor cells: Selection of specific antibodies from single–chain $F_v$ fusion phage libraries", Xiaohong Cai et al., *Proc. Natl. Acad. Sci. USA*, vol. 92 (Jul. 1995) pp. 6537–6541.

"Epithelial–to–mesenchymal change of differentiation. From embryogenetic mechanism to pathological patterns", M. Guarion, *Histol Histopathol*, vol. 10 (1995) pp. 171–184.

"Loss of the Tumorigenic Phenotype with in Vitro, but not in Vivo, Passaging of a Novel Series of Human Bronchial Epithelial Cell Lines: Possible Role of an α5/β1–Integrin–Fibronectin Interaction", Joan H. Schiller et al., *Cancer Research*, vol. 55, (Dec. 15, 1995) pp. 6215–6221.

"In vivo and in vivo regulation of human tumor antigen expression by human recombinant interferons: a review", F. Guadagni et al., *The International Journal of Biological Markers*, vol. 9, No. 1 (1994) pp. 53–60.

"Engineering Subtilisin BPN for Site–Specific Proteolysis", Paul Carter et al., *PROTEINS: Structure, Function and Genetics*, vol. 6 (1989) pp. 240–248.

"Neutralizing Recombinant Human Antibodies to a Conformationa V2– and CD4–Binding Site–Sensitive Epitope of HIV–1 gp120 Isolated by Using an Epitope–Masking Procedure", Henrik J. Ditzel et al., *The Journal of Immunology*, vol. 154 (1995) pp. 893–906.

"Brief Communication: Melanoma–Specific Antibodies Produced in Monkeys by Immunization with Human Melanoma Cell Lines", Richard S. Metzgar et al., *J. Natl Cancer Inst*, vol. 50 (1973) pp. 1065–1068.

"Spectrum of Melanoma Antigens on Cultured Human Malignant Melanoma Cells as Detected by Monkey Antibodies", Shuen–Kuei Liao et al., *Cancer Research*, vol. 39 (Jan. 1979) pp. 183–192.

"Murine monoclonal anti–idiotope antibody breaks unresponsiveness and induces a specific antibody response to human melanoma–associated proteoglycan antigen in cynomolgus monkeys", Panchanon Chattopadhyay et al., *Prac. Natl. Acad. Sci. USA*, vol. 89 (Apr.1992) pp. 2684–2688.

"Human neoplasms elicit multiple specific immune responses in the autologous host", Ugur Sahin et al., *Prac. Natl. Acad. Sci, USA*, vol 92 (Dec. 1995) pp. 11810–11813.

"Human Antibodies with Sub–nanomolar Affinities Isolated from a Large Non–immunized Phage Display Library", Tristan J. Vaughan et al., *Nature Biotechnology*, vol. 14 (Mar. 1996) pp. 309–314.

"Monoclonal antibody—superantigen fusion proteins: Tumor–specific agents for T–cell–based tumor therapy", Mikael Dohlsten et al., *Prac. Natl. Acad. Sci. USA*, vol. 91 (Sep. 1994) pp. 8945–8949.

"Three–dimensional Structure of an Antigen–Antibody Complex at 2.8 åResolution", A. G. Amit et al., *Science*, vol. 233 (Aug. 1986) pp. 747–753.

"Filamentous Fusion Phage: Novel Expression Vectors That Display Cloned Antigens on the Virion Surface", George P. Smith, *Science*, vol. 228 (Jun. 14, 1985) pp. 1315–1317.

"Culture Medium for Enterobacteria", Frederik C. Neidhardt et al., *Journal of Bacteriology*, vol. 119, No. 3 (Sep. 1974) pp. 736–747.

"Characterization of two distinct MHC class II binding sites in the superantigen staphylococcal enterotoxin A", Lars Abrahmsen et al., *The EMBO Journal*, vol. 14, No. 13 (1995) pp. 2978–2986.

Brunette, D.M. et al., "A Rapid Method for the Isolation of L–Cell Surface Membranes Using an Aqueous Two–Phase Polymer System", *J. Membrane Biol.* 5, 215–224 (1971), Springer–Verlag New York, Inc.

Glick, M.C. et al., "Membranes of Animal Cells, III. Amino Acid Incorporation by Isolated Surface Membranes", *Proc. Natl. Acad. Sci*, 63:563–570 (1969), National Academy of Sciences, Washington, D.C.

\* cited by examiner

IDENTIFICATION OF TARGET STRUCTURES E.G. IN VIVO SELECTION METHOD FOR A PHAGE LIBRARY

This is a continuation of International Application No. PCT/SE98/00083, filed Jan. 21, 1998, that designates the United States of America and which claims priority from Swedish Application No. 9700291-9, filed Jan. 31, 1997.

The invention relates to a selection method and the products resulting from the method. More specifically the invention relates to a method for acquiring one or more binding structures against a target structure by means of a first library of one or more binding structures linked to genetic and/or other identifying information.

The phage display technology offers a powerful means to select anti-body fragments with rare specificities from large libraries (1). Antibody libraries from immune, naive and semisynthetic sources of $10^{10}$ diversity and beyond (2–4) can efficiently be examined by the antigen driven selection principle. Typically, for pure protein antigens or haptens, affinity chromatography or panning techniques have been used to achieve enrichment of one hundred to ten-thousand fold by each selection round (5–7). Recently, selection systems based on complex solid-phase antigens such as viable bacterial cells (8), human erythrocytes (9) or other cell suspensions (10–13) have been described. These introduce the use of antibody phage selection to "dissect" a cell surface by cloning antibodies specific to individual cell surface antigens. This can be either random or be directed to a phenotypically defined subset of antigens. One example of a situation where the method described could be highly advantageous is research with the aim to identify new target structures for targeted tumor therapy.

The target tumor phenotype for antibody-guided tumor immunotherapy is typically an invasive/metastatic tumor cell population. Such tumor cells could not be expected to be adequately represented by cultured tumor cell lines primarily selected for proliferation in an artificial culture environment Instead, continued in vitro culture would aggravate phenotypic drift and downregulation of expression of tumor-associated molecules that was sustained in vivo by growth architecture and by the influence of soluble or mesenchymal tissue constituents (15,16). Selection of antibodies for tumor targeting, being critically dependent on the homogenous and abundant expression of the target epitope should preferentially be performed using the authentic tumor cell phenotype during both the antigen driven selection stage and the screening of individual clones.

Thus, successful selection from large libraries of antibody phage specific to known purified antigens has been demonstrated by a number of laboratories. It has also been shown that intact bacterial or mammalian cells, which represent a more complex surface of antigens, can be used for antibody phage selection. However, the use of cell suspensions for phage selection can only generate reagents to cell surface antigens: other components of a tissue such as the extracellular matrix, inflammatory infiltrates, vasculature and components of angiogenesis and intracellular antigens can not be reached by the cell selection approach. In addition, culturing of cells through several passages will introduce selection and phenotypic changes compared to the original cell isolated from a specific tissue environment. Accordingly, there is a demand for a method which could be particularly useful for the identification of antigens which are only expressed in vivo. Such a method should overcome a major limitation of currently used selection protocols.

The purpose of the present invention is to provide an extension of the application of phage technology for the selection of antibodies to complex antigens, thus making it generally applicable to identify antibodies directed against a number of important and/or novel target antigens and epitopes which are not accessible in in vitro culture systems, which would facilitate identification and dissection of antigens which are exclusively expressed in vivo. Of course, the method could generate antibodies to any target structure displayed within the tissue section.

These include antigens whose expression is induced by epithelial cell-mesenchymal cell and cell-matrix interactions, or is tightly regulated spatially or temporally during embryonic development and by a specific pathophysiological process, e.g. tumor progression (14).

A further purpose of the invention is to provide a method with a broad applicability as an analytical tool in studies of cell and tissue development and of antigenic phenotypes associated with tissue pathology of various conditions. Hereby is provided a novel and unique means for a much less biased dissection of specificities among a broad range of tissue expressed antigens analogous to the use of naive antibody libraries for selection of reagents to single antigens (23).

Still a further purpose of the invention is to include in the method by means of negative selection a specific removal of undesired antibodies in order to promote the enrichment of phenotype specific specificities.

In order to achieve these purposes the method according to the invention has obtained the characterizing features of claim 1.

The method according to the invention should have a broad applicability in a variety of research fields (e.g. in the study of embryogenesis, angiogenesis and tumor biology) where novel antibody specificities could be used to define temporal or spatial expression of normal or pathologic tissue phenotypes. The phage selection method described below and applied to selection of melanoma reactive scFv antibodies on sections of metastatic melanoma tissue should thus only be considered and construed as a specific example of the present invention. Thus, the usefulness of the method should not be restricted to identification of tumor associated antigens, but rather be generally applicable for the in situ identification of target structure expression patterns in both normal and pathological tissues.

In order to further explain the invention reference is made to the accompanying drawings in which.

According to the invention one or several binding structures are obtained against a target structure. Such an acquirement of binding structures comprises identifying, producing, chatacterizing, selecting, enriching, or defining the structures. Such binding structures can for example be one or several monoclonal antibodies, one or several proteins, one or several peptides, or one or several organochemical entities. The displayed target structure may include one or several previously uncharacterized and/or unpurified and/or unknown molecules.

The method according to the invention comprises the steps of (a) reacting a first library with the displayed target structure to bind some of the binding structures to the displayed target structure;

(b) separating the displayed target structure and bound binding structures from unbound binding structures;

(c) recovering bound or unbound binding structures; and (d) amplifying bound or unbound binding structures to create a second enriched library of binding structures.

In order to make the method more effective and specific the steps (a) through (c) as well as the steps (a) through (d) can be repeated. The amplification of bound binding structures can be obtained by means of synthesis in growing bacterial cells, PCR (polymerase chain reaction) synthesis, and chemical synthesis. Thus, monoclonal antibody, single-entity, homogenous, uniform and/or other binding structures can be isolated and/or amplified from the second, or third, or fourth etc enriched library.

In contrast to established selection methods based on known and purified target structures, the method according to the invention represents a generally applicable tool for the identification of binding structures directed to displayed target structures which are exclusively displayed in vivo and/or in situ. The displayed target structure is expressed as an authentic phenotypic epitope. The set of displayed target structures can for example be target structures from a whole cell. The displayed target structure can be obtained within a set of displayed target structures representing the authentic in vivo and/or in situ phenotype, and the authentic in vivo and/or in situ phenotype can be the result of a physiological process, a pathological process, a cell and/or tissue development and differentiation, or a drug response, or a naturally occurring degradation process. The pathological process can for example be an inflammation, a secondary tumor deposit, or tumor vasculature. The authentic in vivo and/or in situ phenotype can also be represented by suspended cells from a tissue or body fluid, or such cells pelleted.

The displayed target structure can also be a molecule released from cells, e.g. tumor cells. Such a molecule can be released actively as well as passively.

The displayed target structure can also be located in a cell surface, e.g. a cell membrane, as well as intracellularly or extracellularly of a cell surface. It can also be located intranuclear of a nuclear membrane. Examples of cell associated displayed target structures are different sets of epitopes, ligands, receptors, adhesion molecules, matrix molecules or matrix associated molecules. The displayed target structure can be based on protein, carbohydrate, nucleic acid, or lipid.

The displayed target structure can be obtained within a set of desired as well as undesired displayed target structures. In either case, bound structures or unbound structures are recovered in dependence of the selection intended. A selection system can thus be a combination of a tissue phenotype subtractive approach, i.e. the use of both positive and negative selection, with the use of different types of libraries, e.g. large naive or semi-synthetic libraries.

The target structure displayed in vivo and/or in situ and representing authentic in vivo and/or in situ phenotype is preferably obtained from tissue sections by a histological technique which comprises freezing and/or fixing, and sectioning a tissue sample. Such sections from a frozen tissue sample closely represent the original phenotype of all components at the moment the sample was frozen.

In practice, a tissue is frozen in vivo immediately after surgical removal from a human being or an animal, and the displayed target structure is localized in situ. For the skilled man, there is no principal difference between a frozen tissue section and the same tissue in vivo.

The tissue sections can be pre-treated with enzyme or by chemical means, the enzyme pre-treatment being performed with a protease and/or a polysaccharase, and/or a ribonuclease, and/or a nuclease.

However, the authentic in vivo and/or in situ phenotype can also be obtained from body fluids. The body fluids can for example be blood, suspension of bone marrow, lymph, sperm, cerebrospinal fluid, or secretions from cells. The secretions can be secreted actively as well as passively. Actively secreted secretions are, for example, cytokines.

The first library of binding structure according to the invention can be a naive, synthetic, or semi-synthetic antibody library. It can also be a combinatorial and/or preselected library, the combinatorial and/or preselected library preferably being a library produced by immunization against one or more displayed target structures. However, the combinatorial and/or preselected library can also be a chemical library.

According to the invention, a first library or one or several binding structures is linked to genetic and/or other identifying information. Preferably, the linkage between such binding structures and genetic and/or other identifying information comprises particles of a filamentous phage or of any other virus. The linkage can also comprise polysomes or coded beads, i.e. beads identified by means of coding.

Bound binding structures are recovered by means of cleavage on condition that the cleavage site maintains the amplification ability. Preferably, the cleavage site is between the binding structure and a phage protein. Bound binding structures can also be recovered by disruption of the interaction between binding structure and target structure by chemical denaturation, e.g. chemically based elution such as treatment with an acid or alkaline solution, e.g. triethylamine.

Pasqualini and Ruoslathi (*Nature* 380: 364–366, 1996) disclose a technique for selection of phage particles. Anyhow, this technique is clearly distinguished from the present invention in that it is profoundly restricted to selection towards the intravascularly accessible endothelial cell surface.

EXAMPLES

Unless stated otherwise, tumors used for model experiments originated from the human colon adenocarcinoma cell line Colo 205 (American Type Culture Collection, ATCC, Rockville, Md.), after subcutaneous growth in SCID (severe combined immunodeficiency) mice (Bommice, obtained from Bomholtgaard, Ry, Denmark). Human tumor and normal tissue biopsies and human peripheral blood samples were obtained from Lund University Hospital and Malmö General Hospital, Sweden. Human melanoma cell lines FM3 (kind gift from Dr. Jesper Zeuthen) and FMEX (ATCC) were used in FACS analyses. All tissues were snapfrozen in isopenthane, cooled in liquid nitrogen and stored at 70° C. until cryostat sectioned. Six μm frozen section 3×4 mm wide were mounted on slides and air dried overnight (o/n).

Vectors and scFv Libraries.

The different phagemid vectors, all based on pBR322, were equipped with ampicilin orchloramphenicol resistance genes and a gene for the scFv-M13 pIII (residues 249–406) fusion protein expressed from the lac or the phoA promoter with the secretion directed by either the ompA of the ST II signal peptide. An amber stop codon allowed for production of soluble scFv molecules in non-suppressor strains. The fusion proteins contained either a recognition site for His64Ala subtilisi Ala-Ala-His-Tyr) (17) or Restriction Protease Factor Xa (Ile-Glu-Gly-Arg) situated amino terminal of pIII. An expression plasmid vector carrying a kanamycin resistance gene and the lac promoter was constructed for cassette insertion of scFv fragments in frame fusion with the superantigen staphylococcal enterotoxin A (SEA). The model scFV antibody constructs were derived from the C215 antibody directed to a well characterized epithelial antigen (the affinity for Fab binding is 2.3 nM) (24), and from the D1.3 anti-lysozyme antibody (25). For construction of a scFV antibody library, first strand cDNA was synthesized from total mRNA from lymph nodes of a Cynomolgus Macaque immunized with a suspension of pooled human malignant melanoma metastases mixed with alum adjuvant. Family specific sense primers annealing to the first framework region of human VH (IgG) and VL (lambda, only) genes and antisense primers annealing in the CH1 and CL regions respectively were used for the first PCR. ScFv genes, VL-(Gly4Ser)$_3$-VH, were assembled and inserted into MfuI and XhoI sites of the phagemid vector. The phagemid pool was transformed to E. coli TG-1 cells. Three times $10^7$ primary transformants were spread on minimal-agar plates, grown and pooled before superinfected with M 13K07. helper phage (Promega). Phage rescue and culture of phage libraries and model phage constructs were according to standard techniques (5.6,26).

Selection of Tissue Binding Phage

Tissue sections were air-dried on slides, fixed in acetone at −20° C. for 10 min and rehydrated in 20% fetal calf serum (FCS) in TBS in a humid atmosphere for 1 hour at room temperature. Model or library antibody phage in 100 ml 20% FCS were incubated at 4° C. o/n. The slides were washed 6×10 minutes by gentle agitation in 40 ml TBS in 50 ml Falcon tubes. Depending on the elution method, either of the following steps were performed: (i) Washes for 2×5 min in 50 mM Tris pH 7.6, 1 M NaCl and 2 times in 1×PBS pH 7.6. Phage were diluted with 300 μl 0.1 M triethylamine for 15 min and neutralized with 150 μl 1M Tris pH 7.4. (ii) Washes for 2×5 min in 1 M Nacl, 10 mM Tris-HCl, 6 mM CaCl$_2$, 1 mM EDTA, OH 8.0 (Ala-64 subtilisin buffer) or 100 mM NaCl, 50 mM Tris-HCl, 1 mM CaCl$_2$, pH 8.0 (restriction factor Xa buffer). Bound phage particles were eluted by volume 300 μl 30 mg/ml mutant Ala64-subtilisin for 30 min or volume 300 μl 100 mg/ml restriction factor Xa (New England Biolabs, Beverly, Mass.) for 2 h. All washing and elution steps were perforrmed at room temperature. Phage titres of incubation solutions and eluates were determined by counting antibiotic resistant colony forming units (CFU).

Soluble Antibodies

Single colonies of phagemid infected HB2151 E. coli were transferred to 96 Micro well plates (Nunc, Denmark) and grown at 37° C. in 2×YT supplemented with cm or amp and 2% glucose for 17 h Aliquots were transferred to plates with fresh media with antibiotics, either 2×YT without glucose (lac promoter) or to a defined medium (27) (phoA promoter) and cultured at 30° C. for 17 hours. The Micro well plates were centrifuged and the supernatants were transferred to new plates with an equal volume/well of 1% BSA Similarly scFv-SEA fusion proteins were produced by culturing transformed E. coli UL635 at 30° C. or lower. The integrity of the fusion protein was confirmed by Western blot analysis using 5 μg/ml biotinylated rabbit anti-SEA 1 g. The fusion proteins were quantified in a sandwich type EUSA using rabbit anti-SEA antibodies as capture and biotinylated anti-SEA 1 g as detector antibodies (28).

Immunohistochemistry

Tissue sections first treated as described above were blocked with avidin 15 min and then with biotin 15 min diluted 1/6. Primary antibodies, scFv or scFv-Sea, were incubated for 1 h, followed by secondary 1 mg/ml affinity purified rabbit antibodies to the ATPAKSE tag peptide or 5 mg/ml rabbit antibodies to SEA for 30 min, and biotinylated goat anti-rabbit Mab diluted 1:1000 (Sigma) for 30 min, StreptABComplex HRP (DAKO) diluted 1:110 in 50 mM Tris for 30 min. Between all steps the sections were washed 3 times in TBS. Antibodies, avidin and biotin were diluted in 20% FCS in TBS. The staining reaction was developed for 8 min in 0.5 mg/ml DAB (3,3'-diaminobenzidine tetrahydrochloride, Sigma) dissolved in Tris pH 7.6 with 0.01 percent $H_2O_2$. The slides were rinsed 10 min in tap water and gradually dehydrated in 70–95% ethanol and Xylene before mounting in DPX medium (Sigma).

Flow Cytometry

FM3 or FMEX melanoma cells 200,000 CELLS in 100 ml 1% BSA per tube, were incubated on ice 1 h with the primary antibody scFv K373-SEA (no primary antibody for the negative control), 30 min with 1 mg/ml rabbit anti-SEA 1g and 30 min with fluorescein conjugated donkey anti-rabbit 1 g (Amersham Life Science) diluted 1:100. Two washes in 1% BSA followed each step. The samples were analyzed by FACS (Becton Dikinson).

The colon epithelial tumor specific C215 and the unspecific control D1.3 scFvphagemid constructs were used to develop and evaluate conditions for phage binding washing, and elution. To confirm enrichment capabilities in an unrelated antigen system, the K378 scFv clone selected from a melanoma immune library was included in some experiments.

Example 1

Optimal Phage Concentration

Figure 1:
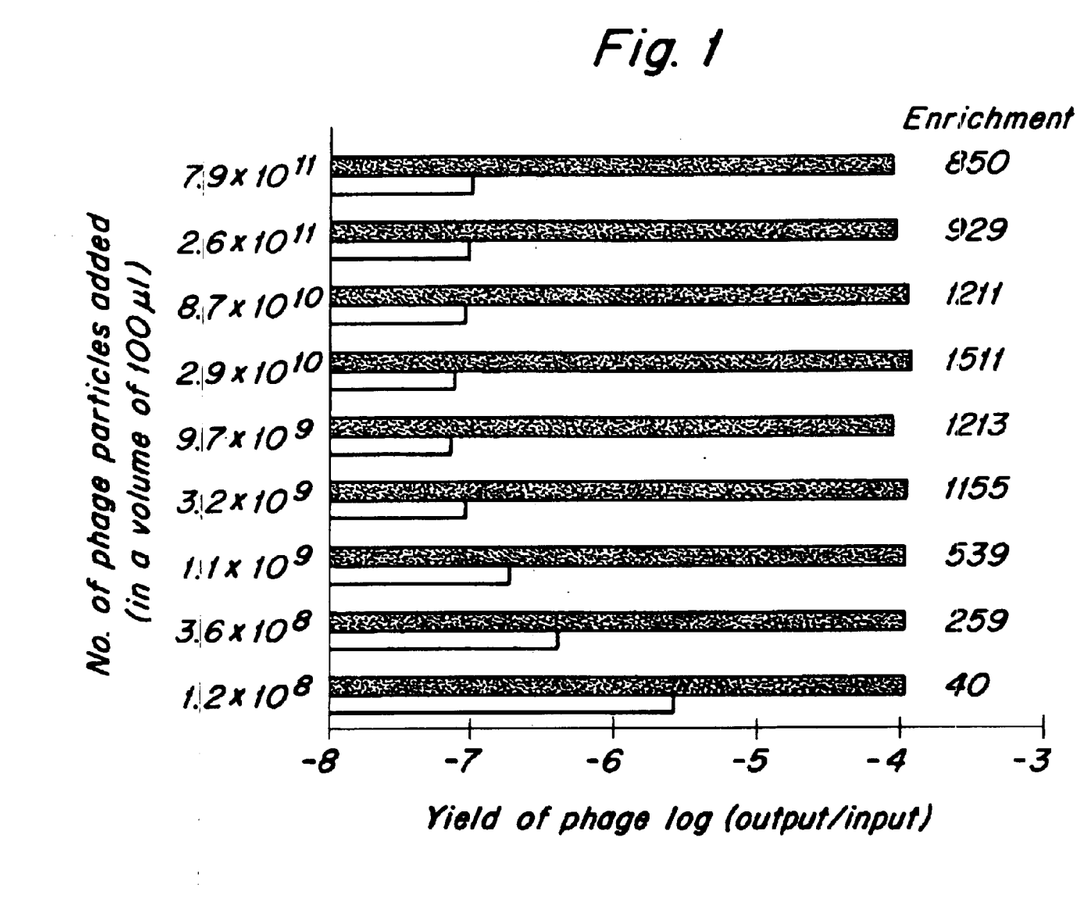
FIG. 1 is a histogram demonstrating yield (output/input) of colony forming units, CFU) of C215 (black bars) and D1.3 (white bars) scFv phage and enrichment of specific phage at various amount of phage added in a volume of 100 $\mu$l. The ratio, 1:15, of the C215 and D1.3 phage in the dilution series was kept constant.

Dilutions of a 15:1 mixture of phage displaying scFv D1.3 ($7.4 \times 10^{11}$) chloramphenicol resistant colony forming units, CFUcm) and scFv C215 ($5.1 \times 10^{10}$ ampicillin resistant CFU, CFUamp) were added to slides holding two 3×4 mm sections of Colo 205 tumor tissue. Non-specific binding of phage (D1.3) remained low (about $10^{-7}$ of input) when total number of phage added (in 100 μl ) exceeded $10^9$. Below that level, non-specific yield increased more than 10×, reducing enrichment from over 1000 × to less than 50×. In contrast the yield of antigen specific C21 5 phage remained equally high ($10^{-4}$) in the range of concentrations tested, demonstrating that more than $5 \times 10^6$ C215 epitopes were available for phage binding under these conditions. (FIG. 1).

Example 2
Antigen Specificity of Phage Enrichment

Figure 5:
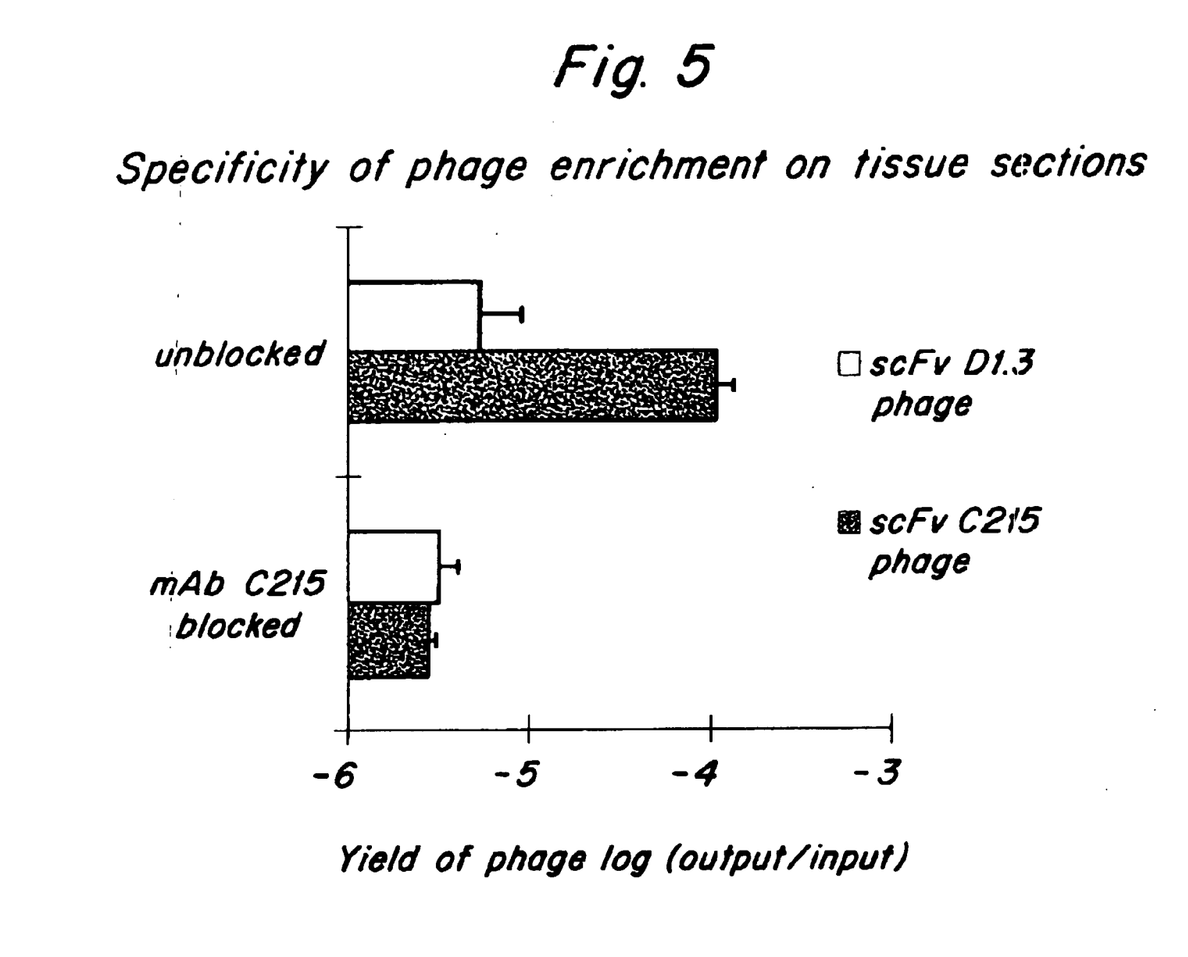
FIG. 5 is a graph showing the specificity of phage enrichment on tissue sections.
Figure 6:
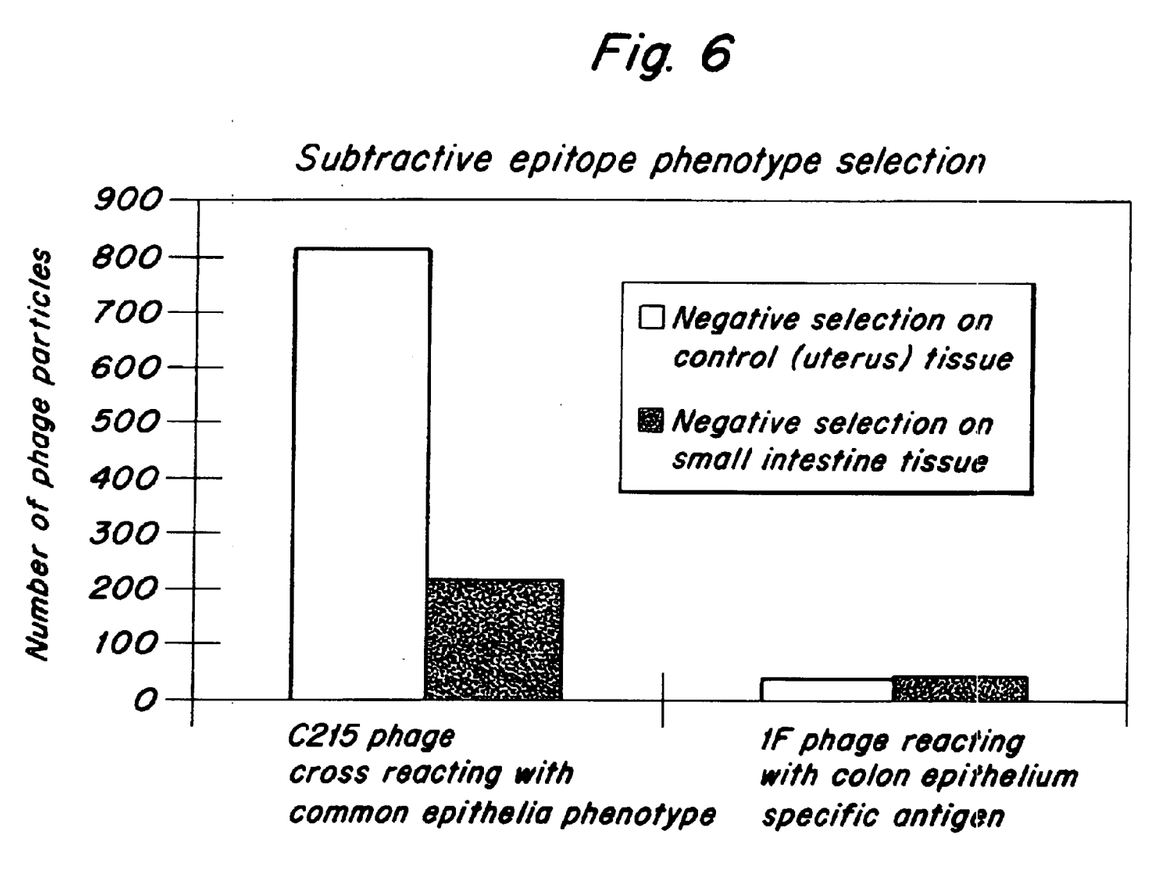
FIG. 6 is a tissue based selection demonstrating the effect of negative selection on reduction on undesired phage antibody specificity.

To demonstrate antigen specificity of phage interaction with the tissue surface, C215 epitopes in sections of colon carcinoma tissue were blocked with an excess of C215 Mab prior to incubation with scFv C215 or scFv D1.3 displaying phage. The yield of specific phage was reduced to the level of the control phage for tissue antigens blocked with Mab, while the yield of D1.3 phage remained unchanged (FIG. 5). Specificity was further demonstrated using crude concentrated culture supernatants containing soluble scFv C215 or the melanoma reactive scFv K(378 antibodies that specifically could inhibit enrichment of the corresponding antigen-specific phage (not shown).

Example 3
Proteolytic Elution of Phage

Proteolytic cleavage sites between the scFv antibody and phage minor coat protein (plll) were introduced to evaluate the efficiency of proteolytic elution. The yield of specific phage. C215 or K378. from homogenous antigen-positive tissues was consistently $1-5 \times 10^{-4}$; no significant difference between the three elution methods, triethylamine, Ala64-subtilisin (17) and blood clotting Factor Xa was demonstrated. In contrast, yield of non-specific phage was always lower with the proteolytic elution methods, by a factor of 1.5 to 4 thus improving enrichment to the same extent (Table 1).

TABLE 1

Proteolytic and triethylamine elution of antibody phage from tissue sections.

| Elution method | Yield of tumor-reactive phage (out/in ± (STD, n = 3)) × $10^{-1}$ | Specificity | Yield of control (out/in ± (STD, n = 3)) × $10^{-1}$ | Enrichment |
|---|---|---|---|---|
| A. Triethylamine | 1.0 ± 0.2 | C215 | 530 ± 340 | 19 |
| Triethylamine C215 blocked** | 0.028 ± 0.002 | " | 380 ± 89 | 1 |
| B. Triethylamine | 3.1 ± 0.5 | " | 130 ± 27 | 238 |
| Ala64-subtilisin | 1.4 ± 0.6 | " | 33 ± 24 | 424 |
| C. Triethylamine | 3.3* | " | 30* | 143 |
| Restriction Factor Xa | 2.9* | " | 60* | 483 |
| D. Triethylamine | 1.3 ± 0.004 | K378 | 9.1 ± 2.0 | 1429 |
| Ala64-subtilisin | 1.5 ± 0.4 | " | 6.1 ± 0.8 | 2459 |

*Mean of duplicates
**20 µg/ml C215 Mab

Figure 2A:
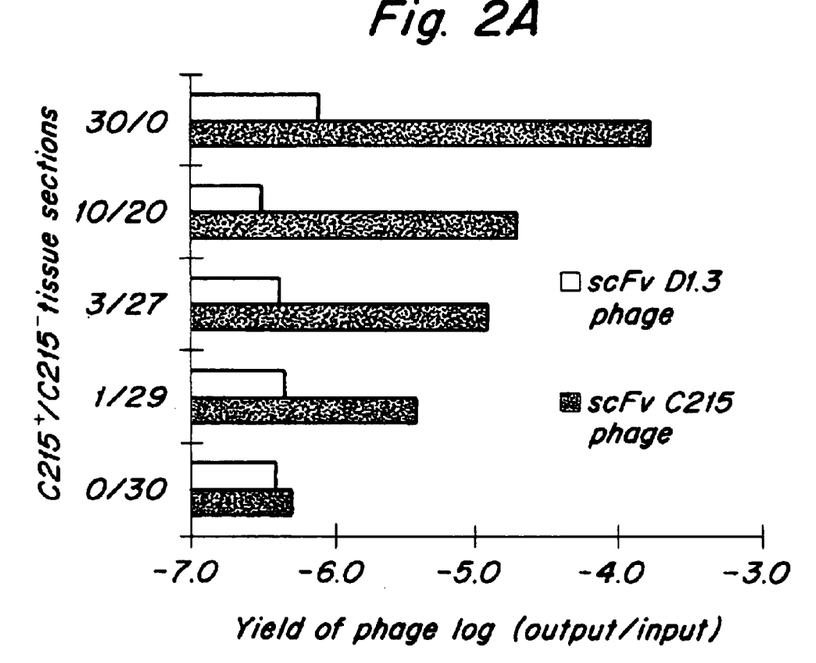
FIG. 2 is a histogram demonstrating correlation of phage yield (A) and specific C215 scFv phage enrichment to the fraction of antigen positive surface area (B) in composite tissue sections.
Figure 2B:
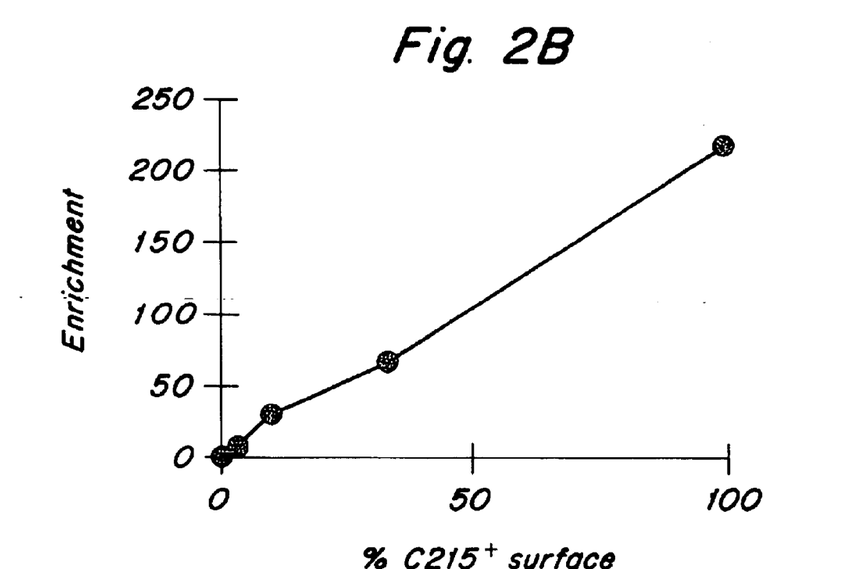

Example 4
Successful Enrichment Depends on the Relative Amount of Antigen Positive Surface Area Most antigens in a tissue section could be expected to distribute over only a fraction of the total tissue surface area (subpopulations of cells/substructures of tissue). As varying antigen distribution in individual tissue section was difficult to reconstruct for model experiments, a mosaic of antigen negative and antigen positive sections was constructed. Slides covered with 30 tissue sections of Colo205 SCID tumor and human spleen in various proportions were produced. A total amount of $3.6 \times 10^8$ scFv C215 phage and $3.0 \times 10^{10}$ control phage was added per slide. The yield of specific phage increased linearly with an increasing number of antigen positive tissue sections, whilst the yield of scFv D1.3 phage was not effected (fluctuated two-fold or less) by the different proportions of tissues within the experiment (FIG. 2). When only antigen-negative (spleen) tissue was applied, the yield of phage of the two populations was similar. Thus, no difference in intrinsic non-specific binding between the phage stocks was seen. Unspecific binding of D1.3 phage did not differ significantly (less than two-fold) between other non-antigen expressing tissue, chosen to represent lipid-rich, epithelial parenchymal and mesenchymal organs (human brain, C. Macaque liver, human spleen and human heart, respectively (data not shown). The effect on enrichment of specific phage by reducing the antigen-expressing surface fraction was also exemplified by a four-fold decrease in yield of specific C215 phage after binding to a primary colorectal cancer biopsy containing epithelial tumor cell areas together with smooth musculature layers and connective tissue of the normal colon components (not shown).

Example 5
Efficiency of Multiple Rounds of Selection

Figure 3A:
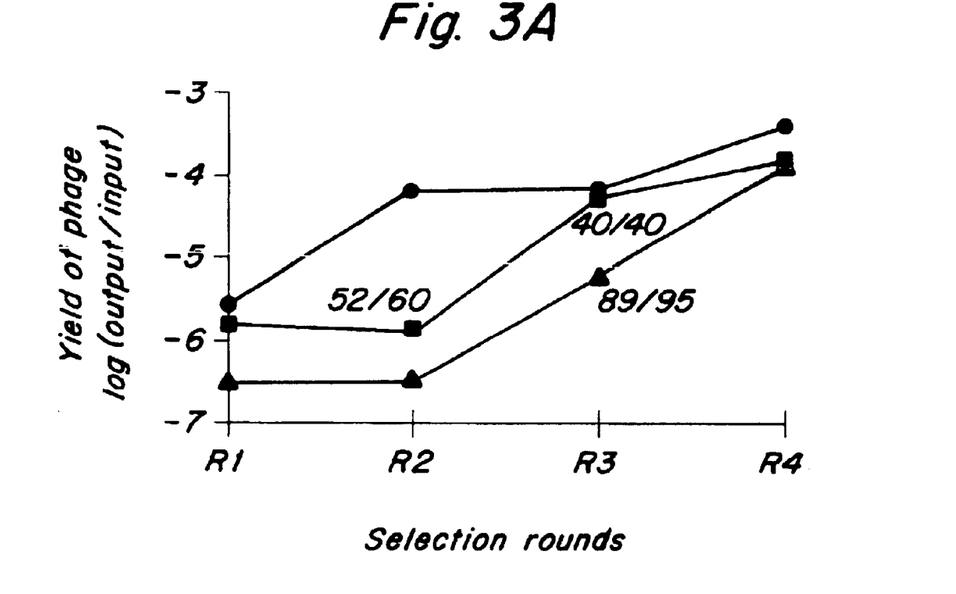
FIG. 3 depicts the yield of phage enrichment after various selection rounds. Diagram (A) shows the effects on phage yield and frequency of C215 scFv producing clones after multiple rounds of tissue-based selection of predetermined frequencies of $10^{-2}$ (circles), $10^{-4}$ (squares) and $10^{-6}$ (triangles) specific C215 phage in mixtures with unspecific D1.3 phage. Diagram (B) shows the increase of phage yield after multiple rounds of selection of immune primate scFv library and internal reference phage D1.3 (triangles) on melanoma tissue sections. In the third selection round, the predominance of scFv clones directed to epitopes common to melanoma samples of two different patients (circle and square) was demonstrated. Phage was eluted by Ala-64 subtilisin digestion.

The first selection round, which is aimed at rescue and enrichment of rare specific phage in a large library, is critically dependent on both the specificity of the procedure, i.e. the enrichment factor and the capacity scale of the system. i.e. the yield of enriched phage populations after selection. In the single pass experiments described, more than $10^4$ phage were rescued after each round of selection, which when assuming an average enrichment factor of 100 times allows enrichment of specificities with original frequencies of one per million in the library. To demonstrate that this could be achieved in the tissue based selection system, four selection rounds were performed with the two model phage (C215:D1.3 phage) mixed in the following proportions, $1:100, 1:10^4$ and $1:10^6$. An increased yield of phage indicated enrichment of specific phage had occurred. After various selection rounds the ratio of specific to unspecific phage was determined by immunohistochemical staining of tissue sections with scFv antibodies produced from randomly picked single clones. From an original frequency of $1:10^6$ in the mixture, 89/95 (94%) clones stained sections with C215 specificity after three selection rounds. This represents a 98-fold enrichment in each pass (FIG. 3A). From the $1:10^4$ mixture, two rounds of selection resulted in a similar enrichment level (average enrichment 93-fold).

Example 6
Library Selection in Melanoma Tissue Sections

Figure 3B:
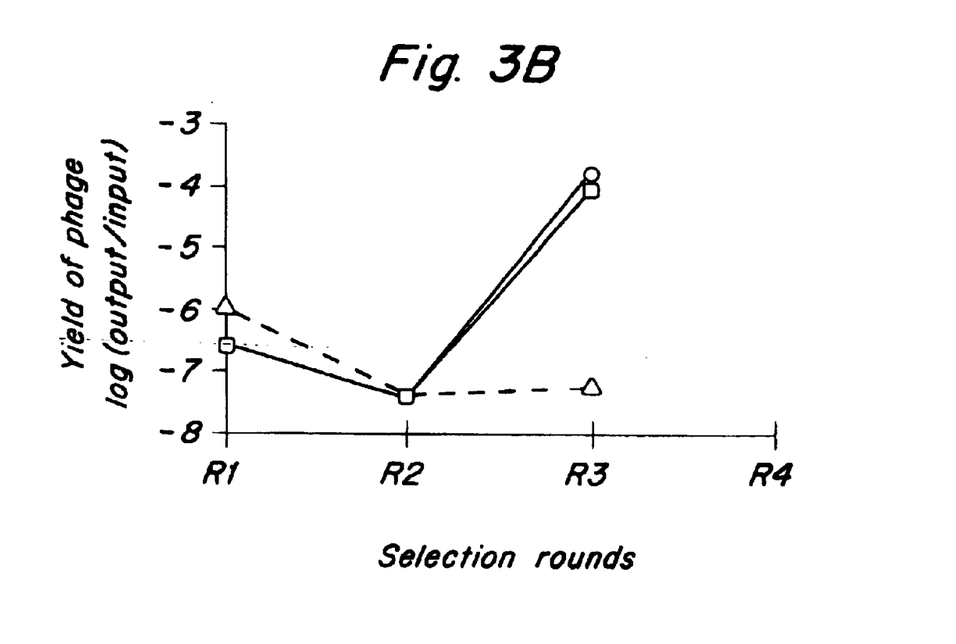
Figure 4A:
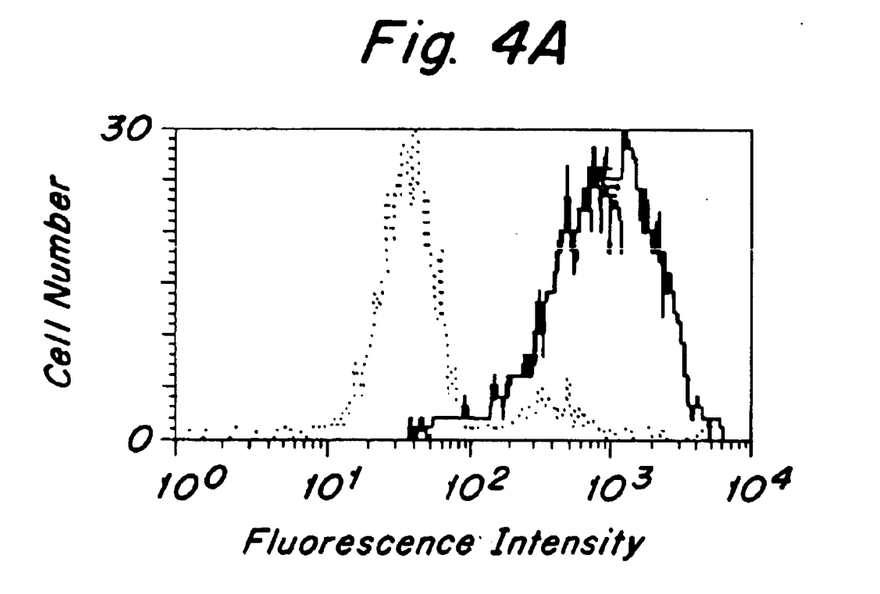
FIG. 4 is a cytofluorograph depicting specific binding of the K373 scFv-SEA fusion protein (solid line) and no primary antibody control (dotted line) to the FM3 human melanoma cell line (a) and lack of binding to human peripheral blood lymphocytes (b).
Figure 4B:
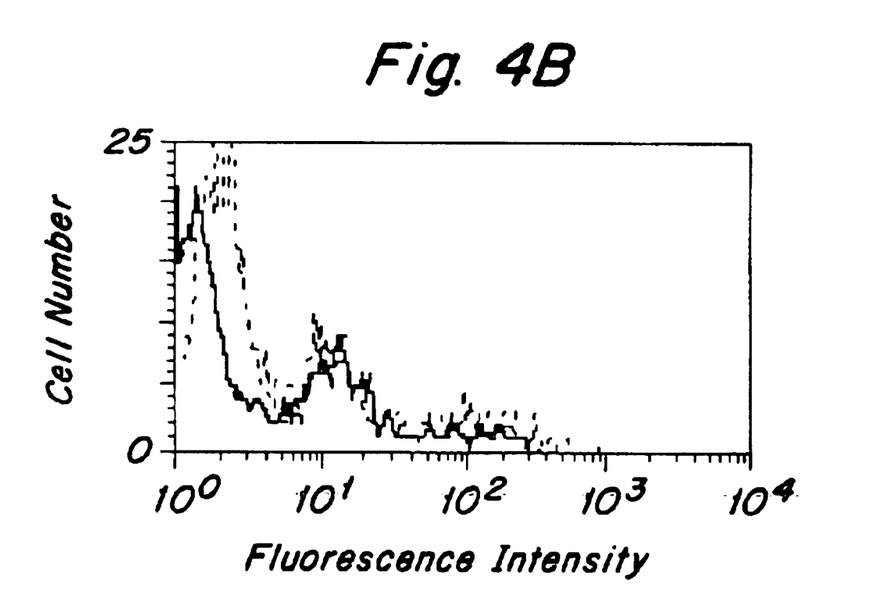

To demonstrate that the tissue-based selection method could be used to identify scFv antibodies towards tissue expressed antigens in an random combinatorial library, a phage library derived from melanoma immunized non-human primates was selected on frozen sections of metastatic melanoma. In each selection round, melanoma tissue from different patients was used to promote enrichment of antibodies to epitopes common to this tumor type and select against antibodies to unique or allotypic markers. After three selection rounds, the yield of phage increased from $10^{-7}$ to $10^4$ (FIG. 3B). Ten clones from the second and third round of selection were randomly picked for PCR and restriction cleavage analysis. From the second round, 3/10 clones and from the third. 10/10 clones had a scFv antibody insert of correct size. Hinfl and Rsal restriction patterns of these inserts revealed that all three clones in the second round, designated K373, K378 and K382, were unique and that all but one clone in the third round had a pattern identical to K378. The predominant representation of the K378 clone in the third round paralleled the increased phage yield at this stage. In a model experiment, the scFv K378 phage was enriched 2490, 575 and 2 times over D1.3 sections of two different melanoma samples and of human spleen (not shown). The scFV antibody genes of K373 and K378 were re-cloned and expressed as fusion proteins with staphylococcal enterotoxin A (SEA) which was used as detection "tag" in immunoassays.

Example 7
The scFv K373-SEA Fusion Protein Binds to Intact Melanoma Cells and Tissue Sections The scFv K373-SEA fusion protein was demonstrated by FACS analyses to bind to cultured cells of the FM3 (FIG. 4A) and FMEX (not shown) melanomas but not to human peripheral blood lymphocytes (FIG. 4B). The intensity of the staining indicated that the epitope was strongly and homogeneously expressed on viable cells and thus demonstrated the cloning of a cell surface reactive antibody phage through the use of a tissue-based selection method. The scFv K373-SEA but not the scFv D1.3-SEA fusion protein strongly and homogeneously stained melanoma cells in section of metastatic melanoma tissue (not shown). By FACS analyses, the K378-SEA fusion protein was found to bind only weakly to FM3 and not to FMEX or PBL. However, in tissue sections of metastatic melanoma this antibody bound strongly to both the melanoma cells and stroma components (not shown).

Example 8

Subtractive Epitope Phenotype Selection

A mixture of filamenteous phage particles displaying the C215 scFv ($3.6\times10^9$ particles) specific for an antigen expressed in all human epithelia, including small intestine and large intestine (colon) and the 1F scFv displaying phage ($1.1\times10^8$), reactive with only colon epithelium, was applied to frozen sections of small intestine or control (uterus) tissue in order to perform a negative selection step. After overnight incubation at +4° C., unbound.

phages in the supernatant were transferred to sections of colon epithelium in order to perform a positive selection step. After overnight incubation at +4° C., sections were washed six times for10 min with 50 mM TRIS, ph 7.6 with 0.15 M NaCl. By incubation with Ala64-subtilisin (33 $\mu$g/ml) at RT, bound particles were eluted and used to infect *E. coli* DH5alphaF' bacterial cells. Infected bacterial cells were grown as single colonies on agar plates. Colonies were counted and used to estimate the number of phage particles in the eluates. By using different antibiotic resistance genes for the two scFv phagemid constructs, the number of phage type could be estimated.

The results (FIG. 6) demonstrate that by negative selection on the crossreactive tissue (small intestine) the number of phage particles of the crossreactive type (C215) could be reduced about 4 times as compared to negative selection on control tissue, while no reduction was recorded for the colon specific phage antibody particles.

By negative selection the frequency of specific phage particles could be enriched 4 times in a single pass phage enrichment experiment as compared to crossreactive phage antibodies. Similarly, phage antibodies can be obtained which define an epitope unique to one tissue and not present in another. Thus, as on small intestine in this case a negative selection specifically removes undesired crossreactive phage antibodies to promote enrichment of phenotype specific specificities.

According to the method of the invention antibody phage can be directly selected in frozen tissue sections. The concentration of phage applied to the tissue sections influenced non-specific binding and efficiency of positive enrichment. Concentrations higher than $5\times10^9/100$ $\mu$l reduced yield of non-specific phage, indicating that a limited number of high-affinity non-specific binding sites could be saturated at these concentrations. This was in contrast to low-affinity non-saturable sites responsible for a relatively constant yield (about $10^{-6}$ of input) of unspecifically. bound phage particles within the high concentration range. Saturation of specific C215 epitopes could not be achieved even at the highest practicable phage concentration, even though only fraction ($<5\times10^6$) of the estimated number of available tissue epitopes ($>10^{10}$) were utilized for phage binding. Phages displaying antibody fragments (about 25 percent of the scFv C215 population by Western blot analysis, not shown) were present in large excess (>2000-fold) as compared to bound and eluted phage. At the highest phage concentration used, corresponding to =0.2 nM of C215 displaying phage, >6 percent of soluble antibody (affinity 2.3 nM) would be bound at equilibrium. This discrepancy suggests that other factors, e.g. steric hindrance and diffusion limitations, will be important to consider for further improvement of binding efficiency and selection capacity.

Proteolytic elution was shown to reduce retrieval of non-specifically bound phage and thus improved enrichment by adding antigen selectivity to the elution process. It will also elute specific phage irrespective of the nature and strength of the antigen-antibody interaction, thereby making the technique more generally applicable.

In single-pass experiments, enrichment of a few hundred times was routinely obtained, as compared to the relatively low enrichment factors (19 at the low end, Table 1) seen before optimization. After optimization, a useful enrichment of antibodies could be achieved even when using heterogenous samples with only 3 percent of antigen-specific surface area, mimicking cell subpopulations/substructures of a tissue (FIG. 2). The million-fold enrichment achieved in three selection rounds on tissue sections was comparable to phage selection using cell suspensions (8, 12) and to use of cultured epithelial cells for enrichment of the same scFv C215 phage (not shown) and to pure antigen systems (1). For a given enrichment factor, the probability of rescuing rare specific phage will directly correlate to the number of eluted phage (which is limited by the total capacity of the selection system); this suggests that the high-end of the concentration range investigated ($10^{10}$–$10^{11}$ CFU per 100 $\mu$l), should optimally be used.

The method according to the invention demonstrates that sections of frozen tissue can be used for "panning" of antibody phage libraries. The specificity of the phage particle interaction with tissue-expressed epitopes was demonstrated by the complete lack of specific enrichment in epitope-blocked and antigen-negative sections, including antigen negative samples of tissues of various histogenetic origin and biochemical composition. Blocking ("masking") of epitopes in a tissue with Mabs or Fab/scFv antibody fragments of already identified specificities may be applied to promote enrichment of novel and less abundant specificities in a library in order to gradually dissect different epitopes of a tissue as shown previously in pure antigen systems (18). By selection of a phage library derived from a human melanoma-immunized primate using metastatic melanoma tissue sections, a clone was identified which stained melanoma cells in tissue sections and defined a cell surface antigen expressed in cultured human melanoma cells but not in human peripheral blood mononuclear cells. The specificity of this cloned antibody (K373) will be further investigated by extended immunohistochemical analysis.

Mabs to melanoma-associated antigens resulting from immunization of non-human primates have previously not been established, although primates have been used previously for tumor-immunization to produce polyclonal antibody reagents (19–21). Moreover, weak humoral and cellular immune responses to the autologous tumor in melanoma patients have clearly demonstrated the presence of melanoma antigens which are immunogenic to humans (22). By the choice of a primate rather than a rodent for immunization with human material, broad antibody responses to various normal human tissue components can be avoided (19). This allows the generation of a greater variety of more discriminating antibody specificities, e.g. to tumor-associated antigens. However, any immunization procedure will be biased by the immune repertoire of the species used.

The present invention describes the development and application of a highly efficient method for the direct selection of a binding structure as an antibody phage towards displayed target structures expressed in vivo and represented by antigens in situ in cryostat tissue sections. In a model system. scFv phage directed towards an epitope on the GA733-2 epithelial glycoprotein expressed in colorectal carcinoma tissue could be specifically enriched by up to 1500 times in single-pass experiments. Enrichment efficiency was directly proportional to the fraction of anitigen positive sections over the total surface area. Sufficient enrichment was achieved at a fraction less than four percent, allowing for the selection of antibodies to subpopulations of cells or to tissue substructures. Successful selection of metastatic melanoma cell surface and cell surface/matrix binding clones from a combinatorial scFv antibody phage library derived from melanoma immunized non-human primates, demonstrated the applicability of the method.

The present invention is applicable not only to human and animal tissues but also to all other living organisms, e.g. plants, fungi, prokaryotes, and other non-mammalian organisms.

References

1. Winter, G., Grifftths, A. D., Hawkins, R. E. and Hoogenboom, H. R. (1994). Making antibodies by phage display technology. *Annu. Rev. Immunol.* 12: 433–455.
2. Waterhouse, P., Griffiths. A. D., Johnson, K. S. and Winter, G. (1993). Combinatorial injection and in vivo recombination: a strategy for making large phage antibody repertoires. *Nucleic. Acids. Res.* 21: 2265–2266.
3. Griffiths, A. D., Williams, S. C., Hartley, O., Tomlinson, I. M., Waterhouse, P., Crosby, W. L., Kontermann, R. E., Jones, P. T., Low, N. M., Allison, T. J. and et al. (1994). Isolation of high affinity human antibodies directly from large synthetic repertoires *EMBO J.* 413: 3245–3260.
4. Hodits, R. A., Nimpf, J., Pfisternueller, D. M., Hiesberger, T., Schneider, W. J., Vaughan, T. J., Johnson, K. S., Haurher. M., Kuechier, E., Winter, G. and et al. (1995). An antibody fragment from a phage display library competes for ligand binding to the low density lipoprotein receptor family and inhibits rhinovirus infection.*J. Biol. Chem.* 270: 24078–24085.
5. McCafferty. J., Griffiths, A. D., Winter, G. and Chiswell, D. J. (1990). Phage antibodies: filamentous phage displaying antibody variable domains. *Nature* 348: 552–554.
6. Barbas, C. F., Kang, A. S., Lerner, R. A. and Benkovic, S. J. (1991). Assembly of combinatorial antibody libraries on phage surfaces: the geneIII site. *Proc. Natl. Acad. Sci. U. S. A.* 88: 7978–7982.
7. Duenas, M. and Borrebaeck, C. A. (1994). Clonal selection and amplification of phage displayed antibodies by linking antigen recognition and phage replication. *Biotechnology* (N. Y). 12: 999–1002.
8. Bradbury A. and Cattaneo, A. (1993). Use of living columns to select specific phage antibodies. *Biotechnology* 11: 1565–1569.
9. Marks. J. D. and Winter, G. (1993). Human antibody fragments specific for human blood group antigens from a phage display library. *Biotechnology* 11: 1145–1149.
10. de Kruif, J., Terstappen, L., Boel, E. and Logtenberg, T.(1995). Rapid selection of cell subpopulation-specific human monoclonal antibodies from a synthetic phage antibody library. *Proc. Natl. Acad. Sci. U. S. A.* 92: 3938–3942.
11. Portolano, S., McLachlan, S. M. and Rapoport, B. (1993). High affinity, thyroid-specific human autoantibodies displayed on the surface of filamentous phage use v genes similar to other autoantibodies. *J. Immunol.* 151: 2839–2851.
12. Kupsch, J.-M., Tidman, N., Newton Bishop, J. A., McKay, I., Leigh, I. and Crowe, J. S. (1995). Generation and selection of monoclonal antibodies, single-chain Fv and antibody fusion phage specific for human melanoma-associated antigens. Melanoma Research 5: 403–411.
13. Cai, X. and Garen, A. (1995). Anti-melanoma antibodies from melanoma patients immunized with genetically modified autologous tumor cells: selection of specific antibodies from single-chain fv fusion phage libraries. *Proc. Natl. Acad. Sci. U. S. A.* 92: 6537–6541.
14. Guarino, M. (1995). Epithelial-to-mesenchymal change of differentiation from embryogenetic mechanism to pathological patterns. *Histol. Histopathol.* 10: 171–184.
15. Schiller, J. H. and Bittner, G. (1995). Loss of the tumorigenic phenotype with in vitro, but not in vivo, passaging of a novel series of human bronchial epithelial cell lines: possible role of an alpha 5/beta 1-integrinfibronectin interaction. *Carcer Res.* 55: 6215–6221.
16. Guadagni, F., Roselli, M., Schlom, J. and Greiner, J. W. (1994). In vitro and in vivo regulation of human tumor antigen expression by human recombinant interferons: a review. *Int. J. Biol. Markers* 9: 53–60.
17. Carter, P., Nilsson, B., Burnier, J. P., Burdick, D. and Wells, J. A. (1989). Engineering subtilisin BPN' for site-specific protedlysis. *Proteins* 6: 240–248.
18. Ditzel. H. J., Binley, J. M., Moore, J. P., Sodroski, J., Sullivan, N., Sawyer, L. S., Hendry, R. M., Yang, W. P., Barbas, C. F. and Burton, D. R. (1995). Neutralizing recombinant human antibodies to a conformational V2-and CD4-binding site-sensitive epitope of HIV-1 gp120 isolated by using an epitope-masking procedure.*J. Immunol.* 154: 893–906.
19. Metzgar, R. S., Bergoc, P. M., Moreno, M. A. and Seigler, H. F. (1973). Brief communication: melanoma-specific antibodies produced in monkeys by immunization with hufmranf melanbma cell lines. *J. Natl. Cancer Inst.* 50: 1065–1068.
20. Liao, S. K, Kwong, P. C., Thompson, J. C and Dent, P. B. (1979). Spectrum of melanoma antigens on cultured human malignant melanoma cells as detected by monkey antibodies. Cancer Res. 39: 183–192.
21. Chattopadhyay, P., Starkey, J., Morrow, W. J. and Raychaudhuri, S. (1992). Murine monoclonal anti-idiotope antibody breaks unresponsiveness and induces a specific antibody response to human melanoma-associated proteoglycan antigen in cynomolgus monkeys. *Proc. Natl. Acad. Sci. U. S. A.* 89: 2684–2688.
22. Sahin. U., Tureci, O., Schmitt, H., Cochiovius, B., Johannes. T., Schmits, R., Stenner, F., Luo, G., Schobert. I. and Pfreundschuh, M. (1995). Human neoplasms elicit multiple specific immune responses in the autologous host. *Proc. Natl. Acad. Sci. U. S. A.* 92: 11810–11813.
23. Vaughan, T. j., Williams, A. J., Pritchard, K., Osborn, J. K., Pope, A. R., Earnshaw, J. C., McCafferty, J., Hodits, R. A., Wilton, J. and Johnson, K. S. (1996). Human antibodies with sub-nanomolar affinities isolated from a large non-immunized phage display library. *Nature Biotechnology* 14: 309–314.
24. Dohlsten, M., Abrahmsen, L, Bjork, P., Lando, P. A., Hedlund, G., Forsberg, G., Brodin, T., Gascoigne, N. R., Forberg, C., Lind, P. and et al. (1994). Monoclonal antibody-superantigen fusion proteins: tumor-specific agents for T-cell-based tumor therapy. *Proc. Natl. Acad. Sci. U. S. A.* 91: 8945–8949.
25. Amit. A. G., Mariuzza, R. A., Phillips, S. E. and Poljak, R. J. (1986). Three-dimensional structure of an antigen-antibody complex at 2.8 A resolution. *Science* 233: 747–753.
26. Smith, G. P. (1985). Filamentous fusion phage: novel expression vectors that display cloned antigens on the virion surface. *Science* 228: 1315–1317.
27. Neidhardt, F. C., Bloch, P. L. and Smith, D. F. (1974). Culture medium for enterobacteria. *J. Bactenol.* 119: 736–747.
28. Abrahmsen, L., Dohlsten, M., Segren. S., Bjork, P., Jonsson, E. and Kalland, T. (1995). Characterization of two distinct MHC class II binding sites in the superantigen staphylococcal enterotoxin a. *EMBO J.* 14: 2978–2986.

What is claimed is:

1. A method to acquire a monoclonal antibody or scFv/Fab antibody fragment against a target structure comprising the steps of:

(A) exposing a first mounted tissue to an initial antibody library or scFv/Fab antibody fragment library, members of the antibody library or members of scFv/Fab antibody fragment library, is linked to a filamentous phage, a virus, a polysome, or a coded bead comprising an antibody- or scFv/Fab antibody fragment-encoding sequence;

(B) eluting directly from the first mounted tissue unbound elements, wherein the unbound elements comprise a first enriched library; and/or
      recovering a second enriched library comprising the filamentous phage, virus, polysome, or coded bead cleaved from bound elements in the first mounted tissue by cleaving the bound elements from the filamentous phage, virus, polysome, or coded bead;

(C) amplifying either the first or second enriched libraries;

(D) exposing the first or second enriched libraries to a second mounted tissue, wherein the second mounted tissue represents a different physiological or pathological state than the first mounted tissue;

(E) eluting directly from the second mounted tissue unbound elements of the second enriched library from the second mounted tissue, wherein the unbound elements comprise a third enriched library; and/or
      recovering a fourth enriched library comprising a filamentous phage, virus, polysome, or coded bead of the first enriched library bound to the second mounted tissue section by cleaving the bound elements from the filamentous phage, virus, polysome, or coded bead of the first enriched library;

(F) amplifying either the third or fourth enriched libraries; and (G) isolating the monoclonal antibody or scFv/Fab antibody fragment from either the third or fourth enriched libraries.

2. The method of claim 1 further comprising repeating steps (A) to (G).

3. The method of claim 1 further comprising repeating steps (D) to (G).

4. The method of claim 1 further comprising repeating steps (A) to (C).

5. The method of claim 1 further comprising the step of comparing binding of the antibody or scFv/Fab antibody fragment to a target structure in the first mounted tissue to binding of the antibody or scFv/Fab fragment to the target structure in the second mounted tissue.

6. The method of claim 5, wherein the binding is specific for a physiological process.

7. The method of claim 6, wherein the physiological process is a pathological process, cell development and differentiation, tissue development and differentiation, a drug response, or a naturally occurring degradation process.

8. The method of claim 7, wherein the pathological process is inflammation, a secondary tumor deposit or tumor vasculature.

9. The method of claim 1, wherein the target structure of the first and second mounted tissues is extracellular or intracellular.

10. The method of claim 9, wherein the intracellular target structure is located intranuclear of a nuclear membrane.

11. The method of claim 9, wherein the extracellular target structure is on the cell surface or a molecule released from a cell.

12. The method of claim 11, wherein the cell is a tumor cell.

13. The method of claim 11, wherein the molecule is released actively or passively.

14. The method of claim 5, wherein the target structure is a ligand, a receptor, an adhesion molecule, a matrix associated molecule or a combination thereof.

15. The method of claim 5, wherein the target structure is a protein, a carbohydrate, a nucleic acid or a lipid.

16. The method of claim 1, wherein the first or second mounted tissue is a frozen tissue section or a fixed tissue section.

17. The method of claim 1, wherein the first or second mounted tissue is pretreated with an enzyme or a chemical.

18. The method of claim 17, wherein the enzyme pretreatment is performed with a protease, a polysaccharase, a ribonuclease, a nuclease or a combination thereof.

19. The method of claim 1, wherein the tissue is bone marrow cells, lymph cells, sperm cells or cells from cerebrospinal fluid.

20. The method of claim 1, wherein the initial library is a combinatorial library.

21. The method of claim 20, wherein the combinatorial library is a naive antibody library, a synthetic antibody library, a semi-synthetic antibody library, or a combinatorial library produced by immunizing against one or more target structures.

22. The method of claim 1, wherein step (C) comprises amplifying the bound or unbound elements using bacterial cells, PCR synthesis or chemical synthesis.

23. The method of claim 1, wherein the monoclonal antibody or scFv/Fab antibody fragment of the initial library is linked to a filamentous phage or virus.

24. The method of claim 1, wherein the the antibody or scFv/Fab antibody fragment or the initial library is linked to a polysome or a coded bead.

25. The method of claim 23, wherein the the antibody or scFv/Fab antibody fragment of the initial library is linked to a filamentous phage.

26. The method of claim 25, wherein the filamentous phage is M13.

27. The method of claim 1, wherein the bound elements recovered in steps (B) or (E) comprise a phage and maintain amplification ability.

28. The method of claim 26, wherein the cleaving of steps (B) or (E) occurs between minor coat protein pIII and the monoclonal antibody or scFV/Fab antibody fragment.

29. The method of claim 1, wherein the cleaving of steps (B) or (E) is a proteolytic cleavage and occurs at a protease recognition site.

30. The method of claim 29, wherein the proteolytic cleavage is performed by Ala64-subtilisin or blood clotting factor Xa.

31. The method of claim 1, wherein the eluting of steps (B) or (E) is a chemical elution.

32. The method of claim 31, wherein the chemical elution is an acid or alkaline elution.

33. The method of claim 32, wherein the alkaline elution is triethylamine elution.

34. The method of claim 1, further comprising repeating steps (A) and (B) to negatively enrich the unbound elements of the first enriched library or to positively enrich the bound elements of the second enriched library.

* * * * *